United States Patent [19]

Kinjo et al.

[11] Patent Number: 4,473,813
[45] Date of Patent: Sep. 25, 1984

[54] HUMIDITY SENSOR WITH IMPROVED PROTECTIVE LAYERING

[75] Inventors: Noriyuki Kinjo; Shuichi Ohara; Toru Sugawara; Shigeki Tsuchitani, all of Hitachi, Japan

[73] Assignee: Hitachi, Ltd., Tokyo, Japan

[21] Appl. No.: 426,087

[22] Filed: Sep. 28, 1982

[30] Foreign Application Priority Data

Sep. 28, 1981 [JP] Japan ................. 56-152200
May 7, 1982 [JP] Japan ................. 57-77191

[51] Int. Cl.³ ............................................. H01L 7/00
[52] U.S. Cl. ..................................... 338/35; 73/336.5; 73/335
[58] Field of Search ................. 422/98; 73/336.5, 29, 73/335, 73; 338/34, 35; 340/602; 324/65 R

[56] References Cited

U.S. PATENT DOCUMENTS

| | | | |
|---|---|---|---|
| 3,073,161 | 1/1963 | Crabtree | 338/35 X |
| 3,167,734 | 1/1965 | Brucker et al. | 338/35 |
| 3,559,456 | 2/1971 | Lomker et al. | 73/336.5 X |
| 3,848,218 | 11/1974 | Wakabayashi et al. | 338/35 |
| 3,864,659 | 2/1975 | Furuuchi et al. | 338/35 |
| 3,891,958 | 6/1975 | Wakabayashi | 338/34 |
| 4,167,725 | 9/1979 | Shimizu et al. | 338/35 |
| 4,245,069 | 1/1981 | Covington | 524/588 |
| 4,386,336 | 5/1983 | Kinomoto et al. | 338/35 |

FOREIGN PATENT DOCUMENTS

| | | | |
|---|---|---|---|
| 50-20781 | 3/1975 | Japan | 338/35 |
| 54-080191 | 6/1979 | Japan | 338/35 |
| 2071323 | 9/1981 | United Kingdom | 73/23 |

Primary Examiner—C. L. Albritton
Assistant Examiner—Christopher N. Sears
Attorney, Agent, or Firm—Antonelli, Terry & Wands

[57] ABSTRACT

The invention relates to a humidity sensor of electric resistance type whose electric resistance changes in accordance with an ambient humidity, characterized by a protective film of silicone resin provided on the surface of a humidity-sensitive material, and to a method for preparing the same. The protective film of silicone resin is formed by applying a varnish of siloxanes to the humidity-sensitive material and subjecting the varnish to reaction. The varnish can be of one-part curing system or two-part curing system, and desirably the reaction of siloxanes is a cross-linking reaction. The formed protective film is not influenced by swelling or shrinking of the humidity-sensitive material, and is prevented from flowing off due to a temperature rise, or from deposition of dusts, etc.

17 Claims, 7 Drawing Figures

HUMIDITY SENSOR WITH IMPROVED PROTECTIVE LAYERING

This invention relates to a humidity sensor and a method for preparing the same, and particularly to a humidity sensor of electric resistance type whose electric resistance changes in accordance with an ambient humidity and a method for preparing the same.

The method for measuring a relative humidity involves a mechanical method and an electrical method. The electrical method has such advantages over the mechanical method that the structure of a measuring device can be made smaller, the response speed of a measuring device is quicker, and the humidity can be more readily convertible to an electric signal. The electrical method uses a humidity-sensitive element of electric resistance type that utilizes a humidity-sensitive characteristic of humidity-sensitive material. The humidity-sensitive element comprises an insulating substrate, a pair of electrodes provided on the insulating substrate, and a layer of humidity-sensitive material covering the electrodes.

The conventional humidity-sensitive materials applicable to the humidity-sensitive element of electric resistance type are given as follows:

(1) Ceramic material,
(2) Electrolyte such as lithium chloride (LiCl), etc.,
(3) Hygroscopic resin containing an electroconductive powder distributed therein; and
(4) Hydrophilic polymer compound or polyelectrolyte.

These humidity-sensitive materials have the following disadvantages:

(1) Water adsorption on a ceramic involves partly irreversible chemical adsorption, and thus a humidity-sensitive element comprising the ceramic humidity-sensitive material is highly influenced by hysteresis and has a poor response speed. When exposed to a highly humid atmosphere for a prolonged time, the element is very liable to undergo degradation.

(2) The electrolyte undergoes deliquescence in a highly humid atmosphere, followed by dilution and releasing. Thus, a humidity-sensitive element comprising the electrolyte humidity-sensitive material has a very short life, also, the a humidity range measurable by one humidity-sensitive element is narrow.

(3) The hygroscopic resin has no humidity-sensitive characteristic in a low humidity atmosphere, and it is hard to obtain uniform distribution of electroconductive powder. Thus, production yield of the humidity-sensitive element is very low with a poor reliability.

(4) The hydrophilic polymer compound or polyelectrolyte has a better humidity-sensitive characteristic than the above three, but is liable to swell or shrink in accordance with the moisture of the atmosphere, because of its high hygroscopic capacity, and the layer of humidity-sensitive material is liable to peel off from the substrate or the electrodes.

Japanese Laid-open Patent Application No. 20781/50 discloses an improvement of the art of said humidity-sensitive material (4), where a highly viscous polysiloxane is applied to the film surface of humidity-sensitive material as a protective film. However, in the humidity sensor thus constructed, dusts, etc. are liable to deposit on the surface of the protective film, and the protective film flows off at a high temperature, so that the thickness of the protective film becomes uneven or the swelling of humidity-sensitive material cannot be prevented. As a result, the humidity-sensitive characteristic is lowered.

An object of the present invention is to provide a humidity sensor with a high endurance to environmental conditions and a high reliability, whose humidity-sensitive characteristic can work stably for a prolonged time.

The present humidity sensor of electric resistance type is a humidity sensor capable of detecting a humidity according to a change in electric resistance corresponding to a change in ambient humidity, characterized firstly by the surface of a humidity-sensitive material film being coated with a protective film of cross-linked silicone resin.

The present humidity sensor is secondly characterized by the protective film of cross-linked silicone resin being a reaction product of siloxanes themselves having reactive groups where R represents a hydrogen atom or an alkyl group.

The method for preparing the present humidity sensor is characterized by applying a varnish of silicone resin to the surface of a humidity-sensitive material film and subjecting it to reaction, thereby forming a protective film.

According to the present invention, a tough protective film of silicone resin is formed on the surface of a humidity-sensitive material film, and thus the humidity-sensitive material film is prevented from direct contact with water droplets in a dew form, or dusts and corrosive gas in the atmosphere or chemicals. That is, deterioration of humidity-sensitive material and lowering of humidity-sensitive material can be firstly prevented, and secondly abnormal swelling in a highly humid atmosphere can be prevented with the result that the stability and reliability as a humidity sensor can be enhanced.

The humidity-sensitive material is not particularly limited, but the said material (4), that is, hydrophilic polymer compound or polyelectrolyte, is preferable owing to its better humidity-sensitive characteristic. Particularly, a latex of polyelectrolyte has the highest reliability.

It is also effective to use an aggregate of fine particles comprising hydrophobic nuclei and cationic surface layers covering the nuclei as a humidity-sensitive material, irrespective of a latex. In that case, any nuclei-forming material and any surface layer-forming material can be used, so far as the nuclei can have a hydrophobic property and the surface layers can have a hydrophilic property with cationic groups. Thus, they are not limited to polymer compounds, or the one and same compound can be used for the nuclei-forming material and the surface layer-forming material. In the case of polymer compound, any of linear polymer compounds and cross-linked compounds can be used. That is, the most appropriate humidity-sensitive material is an aggregate of latex particles whose nuclei are hydrophobic and whose surface layers have cationic groups and are hydrophilic. According to one form of the particles, compounds or groups having a hydrophobic property gather as centers, among the compounds or groups to be formed into individual particles, to form nuclei, and those having a cationic property gather around the nuclei to form surface layers, as in the case of latex particles synthesized in an aqueous solution. They can be copolymers of at least three kinds of monomers. The particles do not always have a distinct boundary between the nuclei and the surface layers, but it is certain that the surfaces layers are more ionic or hydrophilic than the nuclei. In the most cases, ions are uniformly distributed in the surface layers, but it is not objectionable that the particles contain a small amount of ionic or hydrophilic groups in their nuclei. The latex particles synthesized in an aqueous solution spontaneously have a hydrophilic surface, and thus, a humidity-sensitive material for use in the present invention can be simply obtained therefrom.

The latex particles can be prepared usually by copolymerization of cationic vinyl monomers with non-ionic vinyl monomers in water or in an aqueous medium. If necessary, a cationic or non-ionic divinyl type monomer, trivinyl type monomer, or tertravinyl type monomer can be used as a cross-linking agent. A catalyst for copolymerization of two or more kinds of vinyl monomers is not particularly limited, so far as it is applicable to the ordinary vinyl polymerization. Generally, a peroxide polymerization initiator such as potassium persulfate, etc., or an azo compound polymerization initiator such as azobisisobutylamidine hydrochloride, etc. can be used, but the initiator is not limited thereto.

The cationic monomer includes, for example, hydroxides and salts of quaternary ammonium such as 2-methacryloyloxyethyltrimethylammonium, 2-methacryloyloxyethyldimethylethylammonium, 2-methacryloyloxyethyldimethylbutylammonium, 2-methacryloyloxyethyldimethyloctylammonium, 2-methacryloyloxyethyltriethylammonium, 2-methacryloyloxyethyldiethylbutylammonium, 2-methacryloyloxyethyldiethyloctylammonium, 2-acryloyloxyethyltrimethylammonium, 2-acryloyloxyethyldimethyloctylammonium, 2-acryloyloxyethyltriethylammonium, 2-acryloyloxyethyldiethyloctylammonium, 2-hydroxy-3-methacryloyloxypropyltrimethylammonium, 2-hydroxy-3-methacryloyloxypropyltriethylammonium, 2-hydroxy-3-allyloyloxypropyltriethylammonium, 2-hydroxy-3-allyloyloxypropyltrimethylammonium, 2-hydroxy-3-allyloyloxypropyltriethylammonium, vinylbenzyltrimethylammonium, vinylbenzyltriethylammonium, etc.; hydroxides or salts of pyridinium such as N-methyl-4-vinylpyridinium, N-ethyl-4-vinylpyridinium, N-butyl-4-vinylpyridinium, N-ethyl-2-vinylpyridinium, etc.; hydroxides and salts of phosphonium such as vinyltriphenylphosphonium, etc.

Anions for forming salts with these cations include, for example, chloride ion, bromide ion, fluoride ion, iodide ion, acetate ion, nitrate ion, sulfate ion, phosphate ion, etc.

The cationic groups of these cationic monomers and the ammonium groups or pyridinium groups in the divinyl monomers are contained in humidity-sensitive, organic polymer chains, and the counter-anions of these cationic groups are dissociated as charged carriers in accordance with a change in the ambient humidity, whereby the electric resistance of the humidity-sensitive material is changed.

On the other hand, various non-ionic monomers are applicable, for example, methacrylate esters such as methyl methacrylate, hydroxyethyl methacrylate, etc.; acrylate esters such as ethyl acrylate, methyl acrylate, etc.; vinyl monomers such as styrene, vinyl acetate, vinyl chloride, acrylonitrile, etc.; hydrocarbon monomers such as ethylene, propylene, butadiene, isoprene, etc., but the non-ionic monomers are not limited thereto. Any non-ionic monomer can be used, so long as it has no ionic group in its molecule. These non-ionic monomers, when used in the present organic polymer humidity-sensitive material, can give a hydrophobic property to the humidity-sensitive material, and thus contributes to an improvement of moisture resistance. The electrical resistance of the present humidity-sensitive material can be controlled by changing a mixing ratio of the non-ionic monomer and the cationic monomer in the humidity-sensitive organic polymer chain.

When a cross-linking agent is used in preparing a latex-type humidity-sensitive film, the cross-linking agent is not limited to specific ones, so long as it is a monomer having 2 to 4 vinyl groups. Typical ones are divinylbenzene, diallyl phthalate, ethyleneglycol dimethacrylate, ethyleneglycol diacrylate, methylene bisacrylamide, triallyl isocyanurate, etc.

As the cross-linking agent, a divinyl type monomer having a quaternary ammonium group in its molecule can be also used. The divinyl type monomer can be prepared by reaction of a vinyl monomer having a glycidyl group such as glycidyl methacrylate with a vinyl monomer having a tertiary amino group such as dimethylaminoethyl methacrylate (Japanese Laid-open Patent Application No. 68647/81), or by reaction of a vinyl monomer having an alkyl halide group such as vinylbenzyl chloride with a monomer having a tertiary amino group such as dimethylaminoethyl acrylate. It is possible to use a divinyl type monomer having a pyridinium group in its molecule as a cross-linking agent, and such divinyl type monomer is synthesized by reaction of a vinyl monomer having a pyridine ring such as 4-vinylpyridine with a vinyl monomer having an alkyl halide group such as allyl chloride.

Examples of the divinyl type monomer having a quaternary ammonium group in its molecule include a hydroxide or salts of (2-hydroxy-3-methacryloyloxypropyl) (2-methacryloyloxyethyl)dimethylammonium, a hydroxide or salts of (2-hydroxy-3-methacryloyloxypropyl) (2-methacryloyloxyethyl)diethylammonium, a hydroxide or salts of (2-hydroxy-3-acryloyloxypropyl) (2-methacryloyloxyethyl)dimethylammonium, a hydroxide or salts of (2-hydroxy-3-methacryloyloxypropyl) (2-acryloyloxyethyl)dimethylammonium, a hydroxide or salts of (2-hydroxy-3-acryloyloxypropyl) (2-methacryloyloxyethyl)dimethylammonium, a hydroxide or salts of (2-hydroxy-3-allyloyloxypropyl) (2-methacryloyloxyethyl)diethylammonium, a hydroxide or salts of (2-hydroxy-3-allyloyloxypropyl) (2-acryloyloxyethyl) dimethylammonium, a hydroxide or salts of methallyl(2-methacryloyloxyethyl)dimethylammonium, a hydroxide or salts of methallyl (2-methacryloyloxyethyl)diethylammonium, a hydroxide or salts of methallyl (2-acryloyloxyethyl) dimethylammonium, a hydroxide or salts of (vinylbenzyl) (methacryloyloxyethyl)dimethylammonium, a hydroxide or salts of (vinylbenzyl) (methacryloyloxyethyl) diethylammonium, a hydroxide or salts of (2-hydroxy-3-methacryloyloxypropyl) (vinylbenzyl) dimethylammonium, a hydroxide or salts of (2-hydroxy-3-methacryloyloxypropyl) (vinylbenzyl)diethylammonium, a hydroxide or salts of (2-hydroxy-3-acryloyloxypropyl) (vinylbenzyl) dimethylammonium, a hydroxide or salts of (2-hydroxy-3-allyloyloxypropyl) (vinylbenzyl)dimethylammonium, a hydroxide or salts of (2-hydroxy-3-allyloyloxypropyl) (vinylbenzyl)dimethylammonium, a hydroxide or salts of (methallyl) (vinylbenzyl)dimethylammonium, a hydroxide or salts of (methallyl) (vinylbenzyl)diethylammonium, a hydroxide or salts of di(vinylbenzyl)dimethylammonium, a hydroxide or salts of di(vinylbenzyl)diethylammonium, etc. The anions forming salts with these ammoniums include chloride ion, bromide ion, iodide ion, fluoride ion, acetate ion, nitrate ion, sulfate ion, phosphate ion, etc.

Examples of the divinyl type monomer having a pyridinium group in its molecule include a hydroxide or salts of N-(methallyl)-4-vinylpyridinium, a hydroxide or salts of N-(methallyl)-2-vinylpyridinium, a hydroxide or salts of N-(vinylbenzyl)-4-vinylpyridinium, a hydroxide or salts of N-(vinylbenzyl)-2-vinylpyridinium, etc. The anions forming salts with these pyridiniums include chloride ion, bromide ion, iodide ion, fluoride ion, acetate ion, nitrate ion, sulfate ion, phosphate ion, etc.

The divinyl type monomer having a quaternary ammonium group or a pyridinium group in its molecule copolymerizes with the cationic monomer and the non-ionic monomer to form cross-linking bonds, whereby an anti-fouling property, a water resistance, and an organic solvent resistance are given, and a stability for a prolonged time and a reliability are enhanced.

The humidity-sensitive material of latex film has a low resistance, and the humidity sensor using such humidity-sensitive material hardly picks up noise and thus a humidity can be detected with good accuracy.

The protective film of the present humidity sensor is a tough film of a silicone resin where silicones reacted with one another. Cross-linking is particularly desirable for the reaction of silicones themselves, and polymerization can be also carried out after application as a varnish.

As a silicone resin for forming a protective film in the present invention, for example, polycondensation type silicone resin having hydroxyl groups and addition polymerization type silicone resin can be used alone or in their mixture. A desirable temperature for forming a protective film of these silicone resins is not higher than 180° C. Neither disintegration of a latex film structure nor heat deterioration of film itself occurs at that temperature.

Examples of such silicone resins include polymerization products or cross-linking products in a rubbery state, obtained by reaction of siloxanes having such reactive groups as

$$-\underset{|}{\overset{|}{Si}}-OR, \quad -\underset{|}{\overset{|}{Si}}-O-\underset{\parallel}{\overset{}{C}}-R, \quad -\underset{|}{\overset{|}{Si}}-H, \text{ and/or } -\underset{|}{\overset{|}{Si}}-CH=CH_2,$$

wherein R represents a hydrogen atom or an alkyl group, with one another in the presence of a catalyst. For example, the polycondensation type silicone resin is the one containing, α,ω-dihydroxypolydimethylsiloxane and poly(dimethylsiloxane-ω-alkoxymethylsiloxane) as the main components, and the addition polymerization type silicone resin is a commercially available product such as KE 109, produced by Shin-etsu Chemical Co., Ltd., Japan, or the one containing α-ω-divinylpolydimethylsiloxane and poly(methylsiloxane-ω-dimethylsiloxane) as the major components.

Typical patterns of cross-linking reaction of silicone resins are given below:

(A)

B

The patterns (A) and (B) show a two-part cure system, and the pattern (C) a one-part cure system. The raw material siloxane is not limited thereto, and a varnish containing at least two kinds of siloxanes can be used as a raw material.

By forming a protective film of silicone resin on the surface of humidity-sensitive material surface, firstly the humidity-sensitive material film can be prevented from direct contact with water droplets in a dew form, dusts or corrosive gas in the atmosphere, or chemicals, thereby preventing deterioration of humidity-sensitive material and lowering of humidity-sensitive characteristic. Secondly, abnormal swelling in a highly humid atmosphere can be prevented, thereby improving a stability and a reliability as a humidity sensor. Thirdly, the protective film is soft and rich in elongation, and thus can relax the stress due to the swelling or shrinkage caused by absorption and desorption of moisture by the humidity-sensitive material. Fourthly, the protective film is cross-linked and thus never undergoes flowing, even if exposed to a high humidity and/or for a prolonged time.

The thickness of the protective film is not particularly limited, but not more than 20 μm is preferable from the viewpoint of a response of humidity sensor.

The structure of the most appropriate humidity sensor for the present invention comprises an insulating substrate, a pair of electrodes provided on the substrate, connection terminals for connecting the ends of the electrodes to lead wires, a humidity-sensitive material film provided on the upper surface of the insulating substrates provided with the electrodes, and a protective film of cross-linked silicone resins provided on the humidity-sensitive film.

A typical method for preparing the present humidity-sensitive sensor is given below. At first, a dispersion of a humidity-sensitive material is applied to the surface of an insulating substrate provided with the electrodes. The dispersion of a humidity-sensitive material is a latex in dispersion of particles of a humidity-sensitive material obtained by copolymerization of the said vinyl monomers. An appropriate procedure for applying the latex can be selected among spraying, brush coating, dipping, spinner coating, etc. in view of a viscosity, area of substrate, a coating amount, a production rate, etc. After the application of the latex, the substrate is dried, whereby cohesion of latex particles themselves takes place, and a continuous film is obtained. Drying is aeration drying with humidity-controlled air, dry air or nitrogen gas. According to this drying procedure, latex particles are not fractured, so that the particles themselves undergo clean cohesion, for example, without inclusion of bubbles, and a humidity-sensitive film with a good reproducibility can be obtained.

Then, silicone resin is applied in a film form to the thus obtained humidity-sensitive material film. As appropriate procedure for applying the silicone resin can be selected from spraying, brush coating, dipping, spinner coating in view of a viscosity, area of substrate, a coating amount, a production rate, etc. Appropriate conditions for drying or curing the applied varnish of silicone resin are selected in view of the properties of resin. However, conditions such as too high temperature and a prolonged time are not desirable, because heat deterioration of the humidity-sensitive film takes place. They must be limited to a heat hysteresis of not more 180° C. and not more than 10 hours. The procedure of heat-setting of the silicone resin also serves as aging of the humidity-sensitive material, and thus a temperature of 50° C. or higher is desirable. It is desirable in view of stabilizing the characteristics of a humidity sensor to expose the thus ultimately obtained humidity sensor to a high humidity for some hours (for example, 95% RH, 24 hours), if necessary, to conduct aging. The aging effect is particularly remarkable in the case of a humidity-sensitive material using a film formed from the cross-linked latex.

EXAMPLE 1

Figure 1:
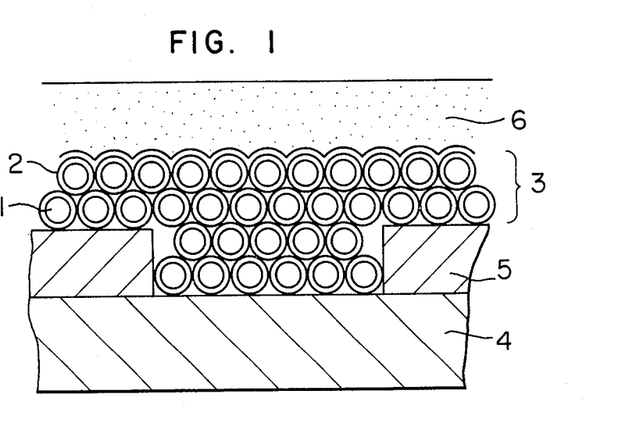
FIG. 1 is a schematic cross-sectional view of a humidity sensor according to one embodiment of the present invention.
Figure 2:
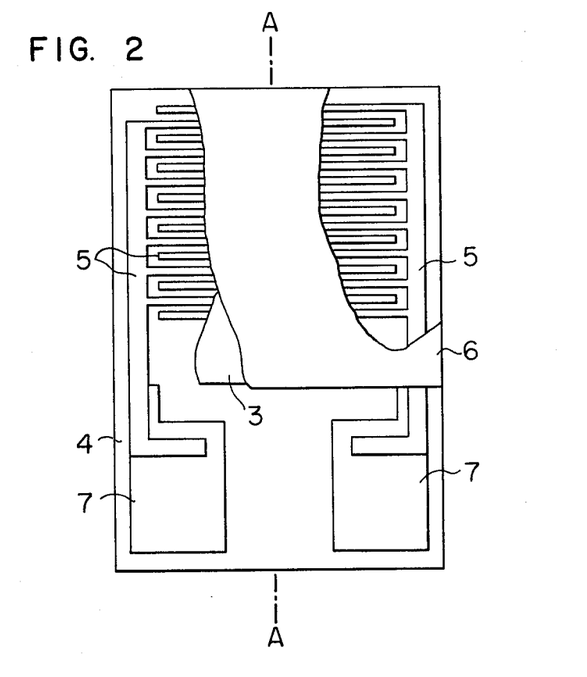
FIG. 2 is a plan view of a humidity sensor according to one embodiment of the present invention.
Figure 3:
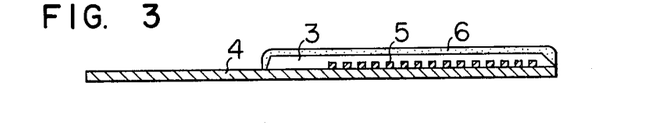
FIG. 3 is a cross-sectional view along the line A—A' of FIG. 2.

(a) Preparation of electrode substrate:

A pair of electrodes 5 are provided on a substrate 4, as shown in FIGS. 1, 2 and 3. Electrodes 5 are in a comb form, as is obvious from FIG. 2, and a pair of electrodes 5 are so arranged that teeth of one electrode can take a staggered position to those of another electrode. Connection terminals 7 at the ends of electrodes are connected to lead wires.

The substrate 4 is an alumina substrate having a dimension of 9.0 mm×13.0 mm×1 mm, and the electrodes 5 are gold electrodes each having a thickness of 10 μm and a width of 20 μm. The gold electrodes are provided on the alumina substrate by screen printing.

(b) Preparation of humidity-sensitive material:

0.2 Moles of methyl methacrylate (MMA) as a hydrophobic monomer, 0.1 mole of 2-methacryloxyethyl-trimethylammonium iodide (METMAF) as a cationic monomer, which also acts as an emulsifier, and 0.001 mole of azobisisobutyl amidine hydrochloride (AIBA) as a polymerization initiator are subjected to emulsion copolymerization in 300 ml of water medium in a nitrogen atmosphere at 60° C. for 10 hours with high speed stirring. As a result, MMA units are incorporated into the particles, whereby a stable latex of particles having trimethylammonium groups existing on their surfaces as a cationic group are obtained. The latex is subjected to purification by dialysis using a cellophane dialysis tube for two months to remove low molecular weight impurities.

(c) Application of humidity-sensitive material to substrate:

The humidity-sensitive material obtained in (b) is applied to the alumina substrate 4 provided with gold electrodes prepared in (a), and dried, whereby a humidity sensor of electric resistance type (Sample 1) is obtained. The film 3 of humidity-sensitive latex thus formed weighs about 5 mg.

The humidity-sensitive film 3 thus formed comprises an aggregate of fine particles each consisting of hydrophobic nucleus 1 and a surface layer 2 having cationic groups. The shape of nucleus 1 is not particularly limited, and thus not only a spherical shape but also a rod shape or a plate shape can be used. However, the humidity-sensitive material is used as a film 3 on the insulating substrate 4, and thus it is desirable that the fine particles can densely fill the spaces between electrodes 5. Thus, it is practically preferable that the fine particles have an average particle size of not more than about 100 μm.

(d) Formation of protective film:

An addition polymerization-type silicone resin (KE 109 made by Shin-etsu Chemical Co., Ltd., Japan) is applied to the surface of humidity-sensitive latex film of the humidity sensor by means of a spinner, and cured at 100° C. for 2 hours, whereby a humidity sensor with a protective film 6 having a thickness of 5 μm (Sample 2) is obtained.

(e) Characteristics of humidity sensors in the present Example:

Humidity-sensitive characteristics of humidity sensors, Sample 1 and Sample 2, are investigated.

Figure 4:
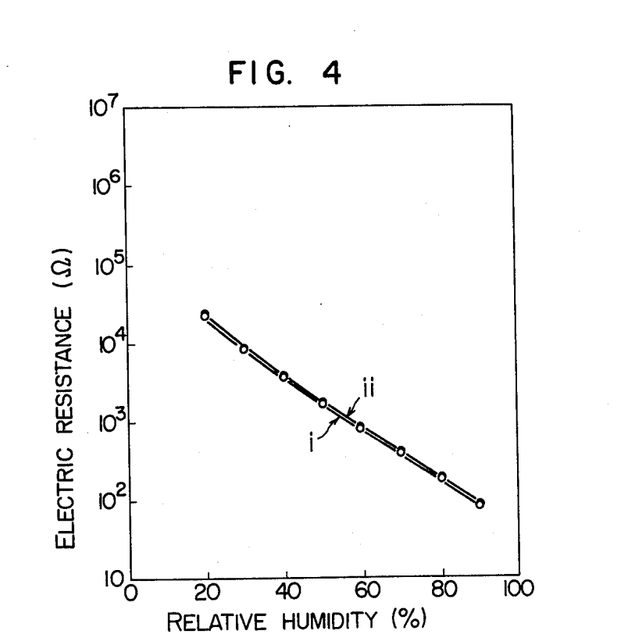
FIG. 4, FIG. 6 and FIG. 7 are characteristic diagrams each showing relations between the relative humidity and the electric resistance according to the embodiment of the present invention and the comparative example.

FIG. 4 is a diagram showing relations between the relative humidity (%) on the axis of abscissa and the electric resistance (Ω) on the axis of ordinate as to the humidity sensors. Curve i shows Sample 1 (Comparative Example) and curve ii shows Sample 2 (embodiment according to the invention). As is apparent from FIG. 4, there is no substantial difference therebetween, and it is found that the formation of a protective film has no influence upon the humidity-sensitive characteristics.

Figure 5:
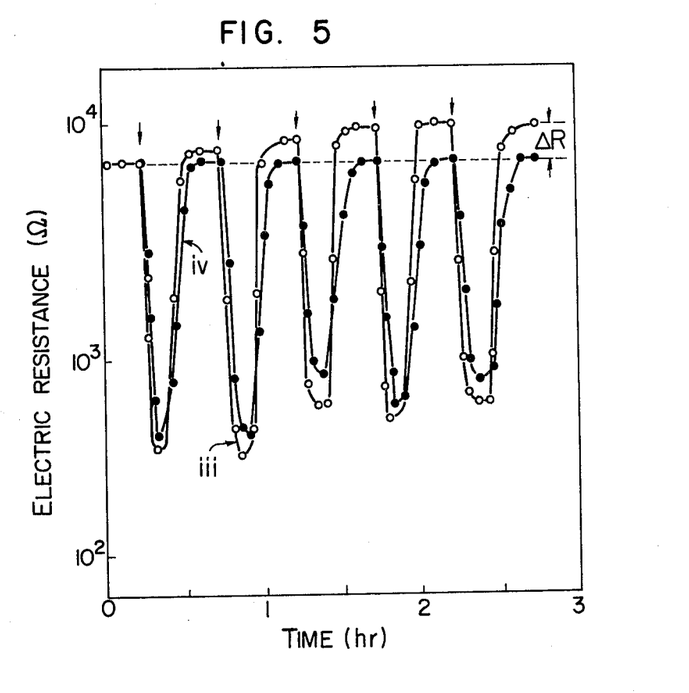
FIG. 5 is a characteristic diagram showing relations between the time and the electric resistance when water droplets are made to fall onto the surfaces of humidity sensors according to the embodiment of the present invention and comparative example at constant time intervals.

Then, a change in characteristics of humidity sensors due to condensation of water is investigated. That is, the two humidity sensors are left standing in an atmosphere of relative humidity (RH) 30%, and 5 droplets each of 0.005 ml are allowed to fall onto the surfaces of the humidity sensors at every 30 minutes to measure a change in electric resistance. The results are shown in FIG. 5. FIG. 5 is a diagram showing relations between the specific time intervals (hour) at which water droplets are allowed to fall onto the surfaces of the humidity sensors on the axis of abscissa and the electric resistance (ω) on the axis of ordinate. Curve iii (—o—) shows Sample 1 (Comparative Example) and curve iv (—●—) shows Sample 2 (embodiment according to the invention), and the arrow marks show the time at which the water droplets are allowed to fall.

As is apparent from FIG. 5, the difference $\Delta R = R - Ro$, where Ro is an initial electric resistance and R is an electric resistance after five fallen water droplets are dried off, is zero in the embodiment according to the invention, whereas ΔR of Comparative Example Sample 1 is remarkably large, that is, the electric resistance changes due to the condensation of water. Thus, it is found that the effect of a protective film is remarkable.

EXAMPLE 2

(a) Preparation of electrode substrate:

Electrode substrates are prepared in the same manner as Example 1 (a).

(b) Preparation of humidity-sensitive material:

0.2 Moles of methyl methacrylate (MMA) and 0.01 mole of methylenebisacrylamide (MBA) as hydrophobic monomers, 0.1 mole of 2-methacryloyloxyethyl-trimethylammonium iodide (METMAI) as a cationic monomer also acting as an emulsifier, and 0.001 mole of azobisisobutylamidine hydrochloride (AIBA) are subjected to emulsion polymerization in 300 ml of water medium in a nitrogen atmosphere at 60° C. for 10 hours with high speed stirring. As a result, MMA units and MBA units are incorporated into the particles, and a stable latex of particles having trimethylammonium groups existing on the surfaces can be obtained. The latex is subjected to purification by dialysis using a cellophane dialysis tube for two months to remove low molecular weight impurities.

(c) Application of humidity-sensitive material to substrate:

Application of humidity-sensitive material to the substrate and the successive drying are carried out in the same manner as in Example 1(c). The film of humidity-sensitive material thus formed weighs about 5 mg. The humidity sensor resulting from this step is referred to as Sample 3.

(d) Formation of protective film:

Polycondensation type silicone resin containing 95 parts by weight of α,ω-dihydroxypolydimethylsiloxane, 6 parts by weight of vinyltrimethoxysilane, and 0.3 parts by weight of dibutyl tin dioctate is applied to the surface of humidity-sensitive latex film of the humidity sensor (Sample 3) by means of a spinner, and subjected to reaction at room temperature and 50% RH for 100 hours, and then to curing at 100° C. for 2 hours, whereby a humidity sensor having a protective film having a thickness of 5 μm (Sample 4) is obtained.

(e) Characteristics of humidity sensors in the present Example:

Humidity-sensitive characteristics of humidity sensors, Sample 3 and Sample 4, are investigated.

Figure 6:
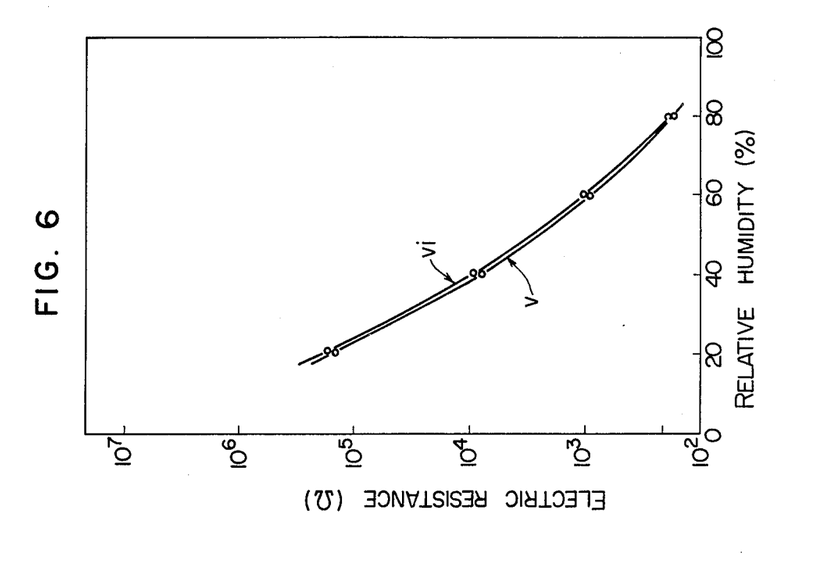

FIG. 6 is a diagram showing relations between the ment according to the invention). As is apparent from FIG. 6, there is no substantial difference therebetween, and it is found that the formation of a protective film gives no influence upon the humidity-sensitive characteristics.

To investigate a stability for a prolonged time, a reliability and resistances to atmosphere of the humidity sensor, the humidity sensors are subjected to various stringent conditions to measure changes in the electric resistance of humidity sensors. The resulting changes in electric resistances from the initial electric resistance are converted to relative humidities by means of curve vi of FIG. 6. The stringent test conditions and results of Samples 3 and 4 are given in Table 1, together with those of other samples of the following Examples 3, 4, 5 and 6. A positive change in relative humidity means that the electric resistance is increased in the stringent test conditions. All the results given in Table 1 are based on the measurement of changes in electric resistance from that of a humidity sensor at 50% RH by the stringent test conditions, and on the successive conversion of the electric resistance to a relative humidity. Each result is an average of 10 samples.

It is said that when a relative humidity changes by more than 10% RH, man can perceive the change in the humidity. A change in the relative humidity by 7-8% RH is a limit value perceivable to man, though dependent upon personal differences. Thus, it seems appropriate to regard 7-8% RH as a drift limit value for a humidity sensor (the drift limit value means a range permitted while still regarding the humidity-sensitive characteristics of a humidity sensor as stable).

TABLE 1

| Stringent test conditions | Ex. 2 Sample 4 | Ex. 2 Comp. Sample 3 | Ex. 3 Sample 6 | Ex. 3 Comp. Sample 5 | Ex. 4 Sample 7 | Ex. 5 Sample 9 | Ex. 6 Sample 10 |
|---|---|---|---|---|---|---|---|
| High temperature exposure test (60° C., 240 hr) | 3.5 % RH | 3.7 % RH | 1.5 % RH | 1.7 % RH | 1.5 % RH | 2.7 % RH | 3.3 % RH |
| Low temperture exposure test (−20° C., 240 hr) | 1.7 % RH | 2.0 % RH | 0.6 % RH | 1.2 % RH | 1.0 % RH | 0.9 % RH | 2.7 % RH |
| High humidity exposure test I (40° C., 90% RH, 240 hr) | 5.5 % RH | 9.0 % RH | 2.5 % RH | 3.3 % RH | 2.8 % RH | 2.7 % RH | 4.5 % RH |
| High humidity exposure test II (55° C., 90% RH, 240 hr) | 7.5 % RH | 12.0 % RH | 5.3 % RH | 5.8 % RH | 6.5 % RH | 5.6 % RH | 6.1 % RH |
| Temp.-humidity cycle test (JIS C5024A, 50 cycles) | 7.0 % RH | 11.0 % RH | 2.0 % RH | 2.5 % RH | 2.5 % RH | 2.1 % RH | 3.9 % RH |
| Dew formation test (falling of water droplets, air drying for 1 hr) | 2.0 % RH | 13.0 % RH | 0.2 % RH | 15.0 % RH | 1.0 % RH | 3.5 % RH | 0.8 % RH |
| Tobacco test (tobacco smoke in a 3.0 l desiccator | 7.0 % RH | 12.0 % RH | 5.4 % RH | 12.0 % RH | 3.1 % RH | 4.8 % RH | 5.0 % RH |
| Salad oil test (dipping in salad oil for 1 min.) | 1.5 % RH | 9.1 % RH | 1.0 % RH | 10.0 % RH | 0.6 % RH | 1.5 % RH | 1.0 % RH |
| SO$_2$ gas test (exposure in 20 ppm SO$_2$ gas for 24 hr.) | 5.0 % RH | 10.1 % RH | 2.8 % RH | 3.2 % RH | 2.0 % RH | 1.0 % RH | 5.0 % RH | relative humidity (%) on the axis of abscissa and the electric resistance (Ω) on the axis of ordinate as to the humidity sensors. Curve v shows Sample 3 (Comparative Example) and curve vi shows Sample 4 (embodi-

EXAMPLE 3

(a) Preparation of electrode substrate:

Electrode substrates are prepared in the same manner as in Example 1(a).

(b) Preparation of humidity-sensitive material:

0.2 Moles of methyl methacrylate as a non-ionic monomer and 0.02 moles of ethyleneglycol dimethallylate as a non-ionic divinyl type monomer are added to a solution of 0.1 mole of 2-methacryloyloxyethyldimethyloctylammonium chloride in 500 ml of distilled water, and then 0.003 moles of azobisisobutylamidine hydrochloride as a polymerization initiator is added thereto. The mixture is subjected to copolymerization reaction in the same manner as in Example 1. As a result, a latex solution of particles of copolymers cross-linked with ethyleneglycol dimethacrylate, uniformly dispersed in water, is obtained. The solution is purified by dialysis to remove low molecular weight impurities.

(c) Application of humidity-sensitive material to substrate:

Application of the humidity-sensitive material and the successive drying are carried out in the same manner as in Example 1(c). The humidity-sensitive film thus formed weighs about 1 mg. The humidity sensor thus prepared in this step is referred to as Sample 5.

(d) Formation of protective film

Addition polymerization-type silicone resin (KE 109, made by Shin-etsu Chemical Co., Ltd., Japan) is applied to the surface of the humidity-sensitive latex film of the humidity sensor by means of a spinner, and cured at 100° C. for 2 hours, whereby a humidity sensor having a protective film having a thickness of 5 μm is obtained (Sample 6).

(e) Characteristics of humidity sensor in the present Example:

Humidity-sensitive characteristics of the humidity sensors, Samples 5 and 6, are investigated.

Figure 7:
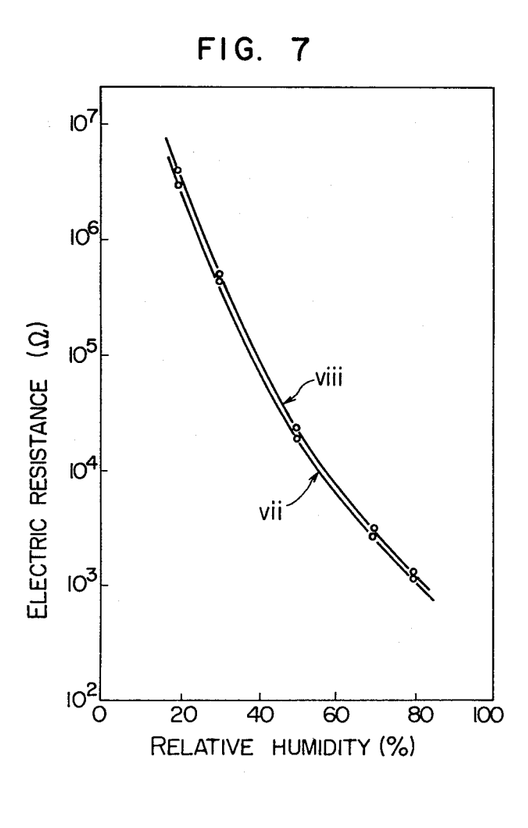

FIG. 7 is a diagram showing relations between the relative humidity (%) on the axis of abscissa and the electric resistance (Ω) on the axis of ordinate, where curve vii shows Sample 5 (Comparative Example) and curve viii shows Sample 6 (embodiment according to the invention). As is apparent from FIG. 7, there is no substantial difference therebetween, and it is found that the formation of a protective film gives no influence upon the humidity-sensitive characteristics.

The humidity sensors of Samples 5 and 6 are left standing in the same stringent atmosphere as in Example 2, and changes in electric resistance are measured and converted to changes in relative humidity by means of the results of FIG. 6. The results are summarized in said Table 1. As is apparent from the results, the humidity sensor of Sample 6 according to the invention has stable characteristics even in the various stringent atmospheres. That is, it is a humidity sensor having good resistances to the atmosphere and a high reliability.

EXAMPLE 4

(a) Preparation of electrode substrate:

Electrode substrates are prepared in the same manner in Example 1(a).

(b) Preparation of humidity-sensitive material:

0.2 Moles of vinylbenzyltrimethylammonium chloride as a cationic monomer and 0.01 mole of divinylbenzyldimethylammonium chloride as a divinyl-type monomer having a quaternary ammonium group in the molecule are dissolved in 500 ml of distilled water, and 0.2 moles of styrene as a non-ionic monomer is added to the resulting aqueous solution. Then, 0.004 moles of azobisisobutylamidine hydrochloride as a polymerization initiator is added thereto, and the mixture is subjected to copolymerization reaction in a nitrogen atmosphere at 60° C. for 10 hours with high speed stirring. In the copolymerization reaction, the vinylbenzoyltrimethylammonium chloride and divinylbenzyldimethylammonium chloride act as an emulsifier in the emulsion polymerization, and thus a latex solution of crosslinked copolymer particles uniformly dispersed in water is obtained. The latex solution is purified by dialysis to remove low molecular weight impurities.

(c) Application of humidity-sensitive material to substrate:

Application of the humidity-sensitive material to the substrate and the successive drying are carried out in the same manner as in Example 1(c). The humidity-sensitive film 3 thus formed weighs about 1 mg.

(d) Formation of protective film:

Addition polymerization-type silicone resin comprising 95 parts by weight of α,ω-divinylpolymethylsiloxane (molecular weight: 34,000), 3 parts by weight of poly(methylsiloxane-ω-dimethylsiloxane) (molecular weight: 1,354), and 0.08 parts by weight of a platinum-based catalyst is applied to the surface of the humidity-sensitive latex film of the humidity sensor by means of a spinner, and subjected to reaction at 100° C. for 2 hours and further at 150° C. for one hour, whereby a humidity sensor having a protective film having a thickness of 5 μm is obtained (Sample 7). Results of changes in electric resistance when the humidity sensor is left standing in the same stringent atmospheres as in Example 2 are shown in said Table 1 after conversion to changes in relative humidity.

EXAMPLE 5

(a) Preparation of electrode substrate:

Electrode substrates are prepared in the same manner as in Example 1(a).

(b) Preparation of humidity-sensitive material:

0.2 Moles of acrylonitrile as a hydrophobic monomer, 0.02 moles of allylglycidyl ether, and 0.02 moles of aminoethyl methacrylate as a cross-linking agent, 0.01 mole of hydroxyethyl methacrylate as a non-ionic monomer giving a graft point, and 0.001 mole of azobisisobutylamidine hydrochloride as a polymerization initiator are added to 500 ml of water, and the mixture is subjected to copolymerization reaction and cross-linking reaction at the same time at a liquid temperature of 70° C. under a nitrogen atmosphere with high speed stirring for 10 hours. Then, 0.01 mole of ceric ammonium nitrate as a graft polymerization initiator and 0.1 mole of 2-methacryloyloxyethyltrimethylammonium bromide as a cationic monomer for grafting are added to the resulting latex, and the mixture is subjected to graft reaction at a liquid temperature of 50° C. in a nitrogen atmosphere with high speed stirring for 6 hours. As a result, a latex of dispersed fine particles whose surface layers are covered by the cationic graft polymer is obtained.

(c) Application of humidity-sensitive material to substrate:

Application of the humidity-sensitive material to the substrate and the successive drying are carried out in the same manner as in Example 1(c). The humidity-sensitive film 3 thus formed weighs about 4 mg. The humidity sensor thus obtained in this step is referred to as Sample 8.

(d) Formation of protective film:

The thus obtained humidity sensor is dipped in silicone resin (KE 102 RTV, made by Shin-etsu Chemical Co., Ltd., Japan, admixed with Catalyst RH) heated to 50° C., and taken up and cured at 90° C. for 4 hours, whereby a humidity sensor having a protective film 6 having a thickness of 7 μm is obtained (Sample 9).

(e) Characteristics of humidity sensors in the present Example:

Results of changes in electric resistance when the humidity sensor (Sample 9) is left standing in the same stringent atmospheres as in Example 2 are shown in said Table 1 after conversion to changes in relative humidity.

EXAMPLE 6

(a) Preparation of electrode substrate:

Electrode substrates are prepared in the same manner as in Example 1(a).

(b) Preparation of humidity-sensitive material:

0.2 Moles of methyl methacrylate as a non-ionic monomer and 0.01 mole of divinylbenzene as a cross-linking agent are added to a solution of 0.1 mole of 2-methacryloyloxyethyldimethylbutylammonium bromide as a cationic monomer in 500 ml of distilled water, and then 0.003 moles of azobisiobutylamidine hydrochloride as a polymerization initiator is added to the mixture. Then, the mixture is subjected to copolymerization reaction in the same manner as in Example 2, whereby a latex solution of copolymer particles uniformly dispersed in water is obtained. The solution is purified by dialysis, and then the counter ions are converted from bromide ions to OH$^-$ by means of a strongly alkaline anion exchange resin (SBR-P, made by Dow Chemical Co., USA).

(c) Application of humidity-sensitive material to substrate:

The latex solution thus obtained is applied to the substrates and dried in the same manner as in Example 1(c). The humidity-sensitive film 3 thus obtained weighs about 2 mg.

(d) Formation of protective film:

Addition polymerization-type silicone resin (KE-106LTV, made by Shin-etsu Chemical Co., Ltd. Japan) is applied to the surface of the humidity-sensitive latex film of the humidity sensor by means of a spinner, and cured at 100° C. for 2 hours, whereby a protective film 6 having a thickness of 4 μm is obtained. The thus obtained humidity sensor is referred to as Sample 10.

(e) Characteristics of the humidity sensor in the present Example:

Results of changes in electric resistance when the humidity sensor (Sample 10) is left standing in the same stringent atmospheres as in Example 2 are shown in said Table 1 after conversion to changes in relative humidity.

EXAMPLE 7

(a) Preparation of electrode substrate:

Electrode substrates are prepared in the same manner as in Example 1(a).

(b) Preparation of humidity-sensitive material:

0.1 Moles of styrene, 0.01 mole of sodium styrenesulfonate also acting as an emulsifier and 0.001 mole of potassium persulfate as a catalyst are subjected to emulsion polymerization in a water medium in a nitrogen atmosphere at 60° C. with high speed stirring for 10 hours, whereby a latex of particles each containing styrene at the inside and sodium styrenesulfonate at the surface is obtained. The latex is subjected to purification by dialysis using a cellophane dialysis tube for 2 months to remove impurities.

(c) Application of humidity-sensitive material to substrate:

The thus obtained humidity-sensitive material (latex) is applied to the substrates in the same manner as in Example 1(c), whereby a humidity sensor is obtained (Sample 11). The humidity-sensitive latex film thus formed weighs 5 mg.

(d) Formation of protective film:

Polycondensation type silicone resin comprising 95 parts by weight of α,ω-dihydroxypolydimethylsiloxane, 6 parts by weight of vinyltrimethoxysilane, and 0.3 parts by weight of dibutyl tin dioctoate is applied to the surface of the humidity-sensitive latex film of the humidity sensor (Sample 11) by means of a spinner, and subjected to reaction at room temperature and 50% RH for 100 hours, and then to curing at 100° C. for 2 hours, whereby a humidity sensor having a protective film 6 having a thickness of 3 μm is obtained (Sample 12).

(e) Characteristics of humidity sensors in the present Example:

The two humidity sensors, Samples 11 and 12, are investigated in the same manner as in Example 1 to find whether the characteristics are changed due to the condensation of water or not. It is found that the electric resistances of Samples 11 and 12 in an atmosphere of 30% RH are substantially equal to each other, i.e. $9.0 \times 10^5 \Omega$. However, ΔR of Sample 12 according to the invention is substantially zero, whereas that of Sample 11 (Comparative Example) is $1.6 \times 10^5 \omega$.

EXAMPLE 8

(a) Preparation of electrode substrate:

Electrode substrates are prepared in the same manner as in Example 1(a).

(b) Preparation of humidity-sensitive material:

Humidity-sensitive material is prepared in the same manner as in Example 5(b).

(c) Application of humidity-sensitive material to substrate:

Application of the humidity-sensitive material to the substrates and the successive drying are carried out in the same manner as in Example 1(c). The humidity sensor thus obtained in this step corresponds to Sample 8.

(d) Formation of protective film:

Addition polymerization type silicone resin comprising 95 parts by weight of α,Ω-divinylpolydimethylsiloxane (molecular weight: 34,000), 3 parts by weight of poly(methylsiloxane-Ω-dimethylsiloxane) (molecular weight: 1,354), and 0.08 parts by weight of a platinum-based catalyst is applied to the surface of the humidity-sensitive latex film of the humidity sensor by means of a spinner, and then subjected to reaction at 100° C. for 2 hours, and further at 150° C. for one hour, whereby a humidity sensor having a protective film 6 having a thickness of 5 μm is obtained (Sample 13).

(e) Characteristics of humidity sensors in the present change with the presence of a protective film. The results are shown in Table 2.

As is apparent from Table 2, ΔR of Samples according to the invention is substantially zero, as compared with the comparative samples, and the effect of the silicone resin protective film 6 is remarkable.

As is also apparent from these samples, the silicone resin protective film 6 for use in the present invention gives no influence upon the proper humidity-sensitive characteristics of humidity-sensitive material, and can prevent an adverse effect by deposition of dusts or condensation of water into dews.

Thus, any other humidity-sensitive material than those illustrated above can be used in the present invention.

TABLE 2

| | Humidity-sensitive material | | | | | Electric resistance at 30% RH (Ω) | Difference in electric resistance (ΔR) (Ω) |
|---|---|---|---|---|---|---|---|
| | Hydrophobic monomer | | Ionic monomer | | Protective film material | | |
| | Species | Moles | Species | Moles | | | |
| Sample 14 | Methyl acrylate | 0.2 | 2-Methacryloxy-ethylbutyldi-methylammonium chloride | 0.05 | Polycondensation type silicone resin (KE 44RTV, made by Shin-etsu Chemical Co., Ltd., Japan) | $7.0 \times 10^5$ | $-0$ |
| Sample 15 | | | | | none | $7.0 \times 10^5$ | $+0.2 \times 10^5$ |
| Sample 16 | Styrene | 0.2 | Vinylbenzyltri-methylammonium chloride | 0.1 | Addition polymerization-type silicone resin* | $1.1 \times 10^4$ | $-0$ |
| Sample 17 | | | | | none | $1.1 \times 10^4$ | $+0.4 \times 10^4$ |
| Sample 18 | Butyl acrylate | 0.1 | Sodium acrylate | 0.04 | addition polymerization-type silicone resin (KE 106 LTV, made by Shin-etsu Chemical Co., Ltd., Japan) | $8.0 \times 10^6$ | $-4$ |
| Sample 19 | | | | | none | $8.0 \times 10^6$ | $+0.1 \times 10^6$ |
| Sample 20 | 4-vinyl pyridine | 0.2 | Sodium acrylate | 0.04 | Addition polymerization-type silicone resin (KE 104Gel, made by Shin-etsu Chemical Co., Ltd., Japan) | $3.0 \times 10^4$ | $-0$ |
| Sample 21 | divinyl-benzene | 0.02 | | | none | $3.0 \times 10^4$ | $+0.5 \times 10^4$ |

*Perpared by mixing α,ω-divinyldimethylpolysiloxane (100 parts by weight), hydrosilyldimethylsiloxane (3 parts by weight), and a platinum-based catalyst (0.1 part by weight) and curing the mixture at 100° C. for 3 hours and at 150° C. for one hour.

Example:

The two humidity sensors, Samples 8 and 13, are investigated in the same manner as in Example 1 to find whether the characteristics change due to the condensation of water or not. It is found that the electrical resistances of Samples 8 and 13 in a 30% RH atmosphere are substantially equal to each other, i.e. $1.2 \times 10^5$ Ω, but ΔR of Sample 13 according to the invention is substantially zero, whereas that of Sample 8 (Comparative Example) is $2.5 \times 10^5$ Ω.

EXAMPLE 9

Samples according to the invention (those having a protective film 6) and Comparative Samples having no protective group 6 are prepared in the same manner as in Examples 1–8, and components for the humidity-sensitive material and the protective film are investigated to find how the characteristics of humidity sensors

What is claimed is:

1. A humidity sensor having a humidity-sensitive material, the electric resistance of the material being changeable in accordance with a change in an ambient humidity, which comprises a protective film of cross-linked silicone resin being provided on the surface of the humidity-sensitive material, the humidity-sensitive material being selected from the group consisting of a hydrophilic polymer compound and a polyelectrolyte.

2. The humidity sensor according to claim 1, wherein the humidity-sensitive material is an aggregate of fine particles, each consisting of a hydrophobic nucleus and a cationic surface layer covering the nucleus.

3. The humidity sensor according to claim 2, wherein the fine particles constituting the humidity-sensitive material are latex particles obtained by copolymerization of a cationic vinyl monomer and a non-ionic vinyl monomer.

4. The humidity sensor according to claim 2, wherein the fine particles constituting the humidity-sensitive material are latex particles obtained by copolymerization of a cationic vinyl monomer, a non-ionic vinyl monomer, and a cross-linking monomer containing vinyl groups.

5. The humidity sensor according to claim 1, 2, 3 or 4, wherein the cross-linked silicone resin is a reaction product of siloxanes themselves having at least one reactive group selected from where R represents a hydrogen atom or an alkyl group.

6. A humidity sensor which comprises an insulating substrate, a pair of electrodes provided on the insulating substrate, connection terminals for connecting the ends of the electrodes to lead wires, and a humidity-sensitive material film provided on the surface of the insulating substrate provided with the electrodes, the improvement in combination therewith comprising a protective film of silicone resin as a reaction product of siloxanes themselves having at least one reactive group selected from where R represents a hydrogen atom or an alkyl group.

7. The humidity sensor according to claim 6, wherein the humidity-sensitive material is selected from the group consisting of a hydrophilic polymer compound and a polyelectrolyte.

8. The humidity sensor according to claim 6, wherein the protective film of the silicone resin is cross-linked.

9. The humidity sensor according to claim 6, 7 or 8, wherein the humidity-sensitive material is an aggregate of fine particles, each consisting of a hydrophobic nucleus and a cationic surface layer covering the nucleus.

10. The humidity sensor according to claim 9, wherein the fine particles constituting the humidity-sensitive material are latex particles obtained by copolymerization of a cationic vinyl monomer and a non-ionic vinyl monomer.

11. The humidity sensor according to claim 10, wherein the fine particles constituting the humidity-sensitive material are latex particles obtained by copolymerization of a cationic vinyl monomer, a non-ionic vinyl monomer, and a cross-linking monomer containing vinyl groups.

12. A humidity sensor having a humidity-sensitive material extending between a pair of electrodes, the electric resistance of the material being changeable in accordance with a change in an ambient humidity, which comprises a protective film of cross-linked silicone resin provided on the surface of the humidity-sensitive material, whereby a protective film that will not flow even if exposed to high humidity, for a long period of time, is provided.

13. The humidity sensor according to claim 1, 6 or 12, wherein said protective film has a thickness of not more than 20 μm.

14. The humidity sensor according to claim 1, 8 or 12, wherein said protective film is formed by curing a varnish coating of silicone resin at a temperature of not more than 180° C.

15. The humidity sensor according to claim 14, having been subjected to an aging treatment at high humidity after the curing.

16. The humidity sensor according to claim 1 or 12, wherein said cross-linked silicone resin is formed from a polycondensation type silicone resin having hydroxyl groups, an addition polymerization type silicone resin, or mixtures thereof.

17. The humidity sensor according to claim 1, 6 or 12, wherein said protective film is in a rubbery state.

* * * * *